US012759955B2

(12) United States Patent
Cassidy et al.

(10) Patent No.: US 12,759,955 B2
(45) Date of Patent: Oct. 13, 2026

(54) PROCESS FOR SYNTHESISING METHANOL

(71) Applicant: JOHNSON MATTHEY DAVY TECHNOLOGIES LIMITED, London (GB)

(72) Inventors: Paul Cassidy, London (GB); Madhan Janardhanan, London (GB)

(73) Assignee: Johnson Matthey Davy Technologies Limited, London (GB)

( * ) Notice: Subject to any disclaimer, the term of this patent is extended or adjusted under 35 U.S.C. 154(b) by 564 days.

(21) Appl. No.: 18/546,194

(22) PCT Filed: Apr. 21, 2022

(86) PCT No.: PCT/GB2022/050998
§ 371 (c)(1),
(2) Date: Aug. 11, 2023

(87) PCT Pub. No.: WO2022/238672
PCT Pub. Date: Nov. 17, 2022

(65) Prior Publication Data

US 2024/0140891 A1 May 2, 2024

(30) Foreign Application Priority Data

May 11, 2021 (GB) ..................................... 2106692

(51) Int. Cl.
*C07C 29/151* (2006.01)
*C01B 3/34* (2006.01)
(Continued)

(52) U.S. Cl.
CPC ............ *C07C 29/1516* (2013.01); *C01B 3/34* (2013.01); *C07C 29/154* (2013.01); *C07C 29/80* (2013.01);
(Continued)

(58) Field of Classification Search
CPC . C07C 29/151; C07C 29/154; C07C 29/1516; C07C 29/1518; C07C 31/04;
(Continued)

(56) References Cited

U.S. PATENT DOCUMENTS 4,321,234 A 3/1982 Ohsaki et al.
4,411,877 A 10/1983 Notman
(Continued)

FOREIGN PATENT DOCUMENTS

WO WO-2005108336 A1 * 11/2005 ......... C07C 29/1518
WO 2006/126017 A1 11/2006
(Continued)

OTHER PUBLICATIONS

English, A., et al., Methanol, Kirk-Othmer Encyclopedia of Chemical Technology, John Wiley & Sons, Inc. (ED). 19 pages, Mar. 16, 2015, https://doi.org/10.1002/0471238961.1305200805140712.a01.pub3 (Year: 2015).*
English A., et al., "Methanol", Mar. 16, 2015 (Mar. 16, 2015), XP055777435, https://doi.org/10.1002/0471238961.1305200805140712.a01.pub3 Retrieved from the Internet: URL: https://doi.org/10.1002/0471238961.1305200805140712.a01.pub3 [retrieved on Feb. 18, 2021] the whole document.

*Primary Examiner* — Yate' K Cutliff
(74) *Attorney, Agent, or Firm* — BakerHostetler

(57) ABSTRACT

A process for synthesising methanol comprising the steps of: passing a hydrocarbon feedstock to a synthesis gas generation unit to form a synthesis gas containing hydrogen, carbon monoxide, carbon dioxide and steam; cooling the synthesis gas in one or more stages of heat exchange and recovering a process condensate from the cooled synthesis gas to form a make-up gas having a stoichiometry value R in the range of 1.70 to 1.94; passing a feed gas comprising the make-up gas to a methanol synthesis unit comprising one or more methanol synthesis reactors containing a copper methanol synthesis catalyst, and; recovering a purge gas and a crude methanol product from the methanol synthesis unit, wherein a hydrogen-rich gas is recovered from the purge gas
(Continued)

and combined with the make-up gas, and a stream of water or steam is added to the feed gas to the methanol synthesis unit.

23 Claims, 4 Drawing Sheets

(51) Int. Cl.
*C07C 29/154* (2006.01)
*C07C 29/80* (2006.01)

(52) U.S. Cl.
CPC .......................... *C01B 2203/0244* (2013.01); *C01B 2203/061* (2013.01); *C01B 2203/1241* (2013.01); *C01B 2203/1258* (2013.01); *C01B 2203/86* (2013.01)

(58) Field of Classification Search
CPC .... C01B 2203/0244; C01B 2203/0233; C01B 2203/061
See application file for complete search history.

(56) References Cited

U.S. PATENT DOCUMENTS

| | | | |
|---|---|---|---|
| 5,827,901 | A | 10/1998 | Konig et al. |
| 7,790,775 | B2 | 9/2010 | Early |
| 8,785,506 | B2 | 7/2014 | Gamlin |
| 2009/0018220 | A1 | 1/2009 | Fitzpatrick |

FOREIGN PATENT DOCUMENTS

| | | | | | |
|---|---|---|---|---|---|
| WO | 2013/144041 | A1 | | 10/2013 | |
| WO | WO-2016180812 | A1 | * | 11/2016 | ............. C07C 31/04 |
| WO | 2017/121980 | A1 | | 7/2017 | |
| WO | 2017/121981 | A1 | | 7/2017 | |
| WO | WO-2019220073 | A1 | * | 11/2019 | ........... C07C 29/151 |
| WO | 2020212681 | A1 | | 10/2020 | |
| WO | WO-2020249923 | A1 | * | 12/2020 | ......... C07C 29/1518 |

* cited by examiner

PROCESS FOR SYNTHESISING METHANOL

CROSS-REFERENCE TO RELATED APPLICATIONS

The present application is the national stage entry of PCT/GB2022/050998, filed Apr. 21, 2022, which claims the benefit of priority to GB 2106692.3, filed May 11, 2021, the entire contents of both of which are incorporated herein by reference.

FIELD

This invention relates to a process for synthesising methanol.

BACKGROUND

Methanol synthesis is generally performed by passing a synthesis gas comprising hydrogen and carbon monoxide and/or carbon dioxide at an elevated temperature and pressure through one or more beds of a methanol synthesis catalyst, which is often a copper-containing composition, in a synthesis reactor. A crude methanol is generally recovered by cooling the product gas stream to below the dew point and separating off the product as a liquid. The crude methanol is typically purified by distillation. The process is often operated in a loop: thus, unreacted gas may be recycled to the synthesis reactor as part of the feed gas via a circulator. Fresh synthesis gas, termed make-up gas, is added to the recycled unreacted gas to form the feed gas stream. A purge stream is often taken from the circulating gas stream to avoid the build-up of inert gasses in the loop.

Methanol synthesis may be described by the following two equations:

$$3H_2+CO_2 \leftrightarrows CH_3OH+H_2O$$

$$2H_2+CO \leftrightarrows CH_3OH$$

There are two stoichiometric values that are commonly used to describe the proportions of the reactants fed to the methanol synthesis reactor. These are R and Z and may be determined from the molar concentrations of the components in the synthesis gas as follows.

$$R=([H_2]-[CO_2])/([CO]+[CO_2])$$

$$Z=[H_2]/(2[CO]+3[CO_2])$$

In addition, for methanol synthesis, it is often useful to determine a value S; being the sum of the $Nm^3/h$ of $H_2$+$Nm^3/h$ of CO in the synthesis gas. S, Z and R may then be linked by the equation:

$$\text{Maximum methanol make } (Nm^3/h)=Z \cdot S/(R+1) \text{ for } Z\leq 1$$

$$\text{Maximum methanol make } (Nm^3/h)=S/(R+1) \text{ for } Z>1$$

The ideal stoichiometric mixture arises when there is enough hydrogen to convert all of the carbon oxides into methanol. This is when R=2 and Z=1. However different synthesis gas generation techniques produce different synthesis gases having different proportions of the reactants.

WO2006126017 (A1) discloses a process for synthesising methanol is described comprising the steps of; (i) reforming a hydrocarbon feedstock and separating water from the resulting reformed gas mixture to generate a make-up gas comprising hydrogen and carbon oxides, said make-up gas mixture having a stoichiometric number, R, defined by the formula; R=([H2]−[CO2])/([CO2]+[CO]) of less than 2.0, (ii) combining said make-up gas with an unreacted synthesis gas to form a synthesis gas mixture, (iii) passing the synthesis gas mixture at elevated temperature and pressure through a bed of methanol synthesis catalyst to generate a product stream comprising methanol and unreacted synthesis gas, (iv) cooling said product stream to recover a crude methanol stream from said unreacted synthesis gas, (v) removing a portion of said unreacted synthesis gas as a purge gas, and (vi) feeding the remaining unreacted synthesis gas to step (ii), characterized in that hydrogen is recovered from at least a portion of said purge gas and a portion of said make-up gas, and the recovered hydrogen is included in the synthesis gas mixture. While effective for balancing the feed gas stoichiometry, in this process, and other processes with hydrogen recovery, the carbon-rich gas recovered after hydrogen separation often has a calorific value that exceeds the fuel demand of the plant. This has the effect of lowering the production of methanol.

WO2016180812 (A1) discloses a process for methanol production from synthesis gas, which comprises the steps of providing a make-up gas containing hydrogen and carbon monoxide, in which the content of carbon dioxide is less than 0.1 mole %, mixing the make-up gas with a hydrogen-rich recycle gas and passing the gas mixture to a methanol synthesis reactor, optionally via a sulfur guard, and subjecting the effluent from the synthesis reactor to a separation step, thereby providing crude methanol and the hydrogen-rich recycle gas, the customary addition of carbon dioxide to the make-up gas is replaced by addition of water in an amount of 0.1 to 5 mole %. Carbon dioxide is necessary in order to achieve acceptable loop efficiency; therefore this process adds water in place of carbon dioxide to the make-up gas in order to compensate for its low carbon dioxide content by promoting the water-gas shift reaction, which occurs over the methanol synthesis catalyst. The water-gas shift reaction may be described by the following equation:

$$CO+H_2O \leftrightarrows CO_2+H_2$$

SUMMARY

The Applicant has discovered that the addition of water or steam to a make-up gas promotes the water gas shift reaction across the methanol synthesis catalyst resulting in a higher amount of carbon dioxide and hydrogen in the methanol converter effluent, which, in turn, increases the amount of dissolved carbon dioxide in the crude methanol product. This has the effect that the purge gas recovered from the loop has a greater concentration of hydrogen and carbon dioxide, rather than carbon monoxide, which results in more hydrogen recycle and a carbon-rich off gas from the hydrogen recovery unit that does not overwhelm the fuel requirement for the process.

DETAILED DESCRIPTION

Figure 1:
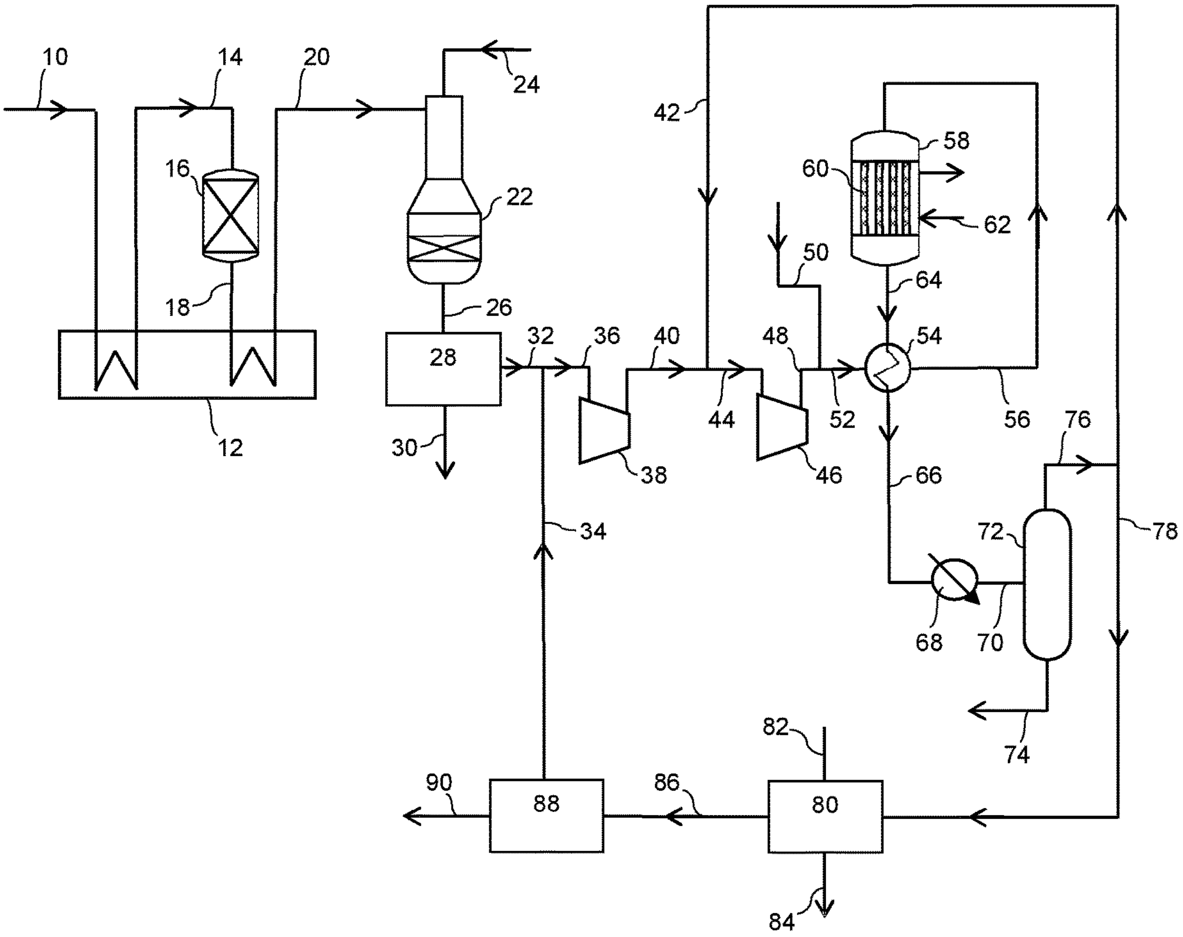
FIG. 1 depicts a process according to one embodiment of the invention.

Accordingly, the invention provides a process for synthesising methanol comprising the steps of: (i) passing a hydrocarbon feedstock to a synthesis gas generation unit to form a synthesis gas containing hydrogen, carbon monoxide, carbon dioxide and steam; (ii) cooling the synthesis gas in one or more stages of heat exchange and recovering a process condensate from the cooled synthesis gas to form a make-up gas having a stoichiometry value R in the range of 1.70 to 1.94; (iii) passing a feed gas comprising the make-up gas to a methanol synthesis unit comprising one or more methanol synthesis reactors containing a copper methanol synthesis catalyst, and; (iv) recovering a purge gas and a crude methanol product from the methanol synthesis unit, wherein a hydrogen-rich gas is recovered from the purge gas and combined with the make-up gas, and a stream of water or steam is added to the feed gas to the methanol synthesis unit.

The stoichiometry value R is defined as $R \equiv ([H_2]-[CO_2])/([CO]+[CO_2])$ and may be determined by calculation or measurement of the concentrations of the hydrogen, carbon monoxide and carbon dioxide in the make-up gas.

The synthesis gas generation unit may comprise a partial oxidation unit having one or more catalytic, or non-catalytic, partial oxidation vessels, or a gasification unit containing one or more gasifiers, or a reforming unit comprising one of more catalytic steam reformers. Whereas any synthesis gas generation unit that produces a make-up gas having a stoichiometry value, R, in the range of 1.70 to 1.94, the present invention is of particular utility where the synthesis gas generation unit comprises an autothermal reformer (ATR). The synthesis gas generation unit may comprise an autothermal reformer as the sole reformer, to which the hydrocarbon feedstock, optionally mixed with steam, may be fed. However, in a preferred arrangement, the synthesis gas generation unit comprises an adiabatic pre-reformer and autothermal reformer connected in series. A mixture of the hydrocarbon feedstock and steam are fed to the pre-reformer to convert C2+ hydrocarbons to methane and form a pre-reformed gas mixture containing hydrogen, steam, carbon monoxide, carbon dioxide and methane, which is fed to the autothermal reformer. The inclusion of a pre-reformer upstream of the autothermal reformer allows a greater amount of heat to be put into the process upstream of the ATR and allows a higher R value to be achieved at the ATR exit than use of an ATR alone.

Where the synthesis gas generation unit includes a gasification unit, the hydrocarbon feedstock may be carbonaceous, e.g. coal, biomass or municipal waste. Where the synthesis gas generation unit includes a reforming unit, the hydrocarbon feedstock may be any gaseous or low boiling hydrocarbon-containing feedstock such as natural gas, associated gas, LPG, petroleum distillate or naphtha. It is preferably methane, associated gas or natural gas containing a substantial proportion, e.g. over 85% v/v methane. Natural gas is an especially preferred feedstock. The feedstock may be available at a suitable pressure or may be compressed to a suitable pressure, typically in the range 10-100 bar abs.

If the hydrocarbon feedstock contains sulphur compounds, before or after compression, the feedstock may be subjected to desulphurisation, e.g. hydrodesulphurisation using Co or Ni catalysts and absorption of hydrogen sulphide using a suitable absorbent, e.g. a zinc oxide bed. To facilitate this and/or reduce the risk of soot formation in the synthesis gas generation unit, hydrogen may be added to the hydrocarbon feedstock. The amount of hydrogen in the resulting mixed gas stream may be in the range 1-20% vol, but is preferably in the range 1-10%, more preferably in the range 1-5%. In a preferred embodiment a portion of the hydrogen-rich gas is mixed with the hydrocarbon feed stream. The hydrogen stream may be combined with the hydrocarbon upstream and/or downstream of any hydrodesulphurisation stage.

If desired, in addition to the addition of the hydrogen-rich gas, an external source of import hydrogen may be added to the make-up gas.

Where the synthesis gas generation unit comprises a pre-reformer or other steam reformer, the hydrocarbon feedstock is mixed with steam: this steam introduction may be effected by direct injection of steam and/or by saturation of the hydrocarbon feedstock by contact of the latter with a stream of heated water in a saturator. One or more saturators may be used. If desired, a portion of the hydrocarbon feedstock may bypass the steam addition, e.g. the saturator. The amount of steam introduced may be such as to give a steam ratio of 0.3 to 3, i.e. 0.3 to 3 moles of steam per gram atom of hydrocarbon carbon in the hydrocarbon feedstock. It is preferred that the steam to carbon ratio is ≤1.5:1, more preferably in the range 0.3 to 0.9:1. The hydrocarbon/steam mixture may then be pre-heated prior to reforming, e.g. in the pre-reformer. This may be achieved by using a fired heater. The fired heater may be heated by combustion of a portion of the hydrocarbon feedstock, typically with waste fuel gases separated from downstream processing, which preferably includes a portion of a carbon-rich gas obtained after recovery of the hydrogen-rich gas. The resultant hydrocarbon feedstock/steam mixture may then be subjected to reforming in the synthesis gas generation unit.

In a preferred arrangement, reforming of the hydrocarbon feedstock is performed in two stages in series, comprising a first stage of adiabatic pre-reforming and a second stage of autothermal reforming. In such a process, the hydrocarbon/steam mixture, is desirably heated to a temperature in the range 300-650° C., and then passed adiabatically through a bed of a suitable steam reforming catalyst, usually a catalyst having a high nickel content, for example above 40% by weight. During such an adiabatic steam reforming step, any hydrocarbons higher than methane react with steam to give a mixture of methane, carbon oxides and hydrogen. The use of such an adiabatic reforming step, commonly termed pre-reforming, is desirable to ensure that the feed to the autothermal reformer contains no hydrocarbons higher than methane and also contains a significant amount of hydrogen. This may be desirable in cases of low steam to carbon ratio feeds in order to minimise the risk of soot formation in the autothermal reformer. The pre-reformed gas, which comprises methane, hydrogen, steam, and carbon oxides, is then fed, optionally after addition of steam and/or a hydrogen-containing stream, to an autothermal reformer in which it is subjected to autothermal reforming. If desired the temperature and/or pressure of the pre-reformed gas may be adjusted before feeding it to the autothermal reformer. The steam reforming reactions are endothermic and therefore, especially where natural gas is used as the hydrocarbon feedstock, it may be desirable to re-heat the pre-reformed gas mixture to the autothermal reformer inlet temperature. If the pre-reformed gas is heated, this may conveniently also be performed in the fired heater used to pre-heat the feed to the pre-reformer.

An autothermal reformer will generally comprise a burner disposed near the top of the reformer, to which is fed the hydrocarbon feedstock or pre-reformed gas and an oxygen-containing gas, a combustion zone beneath the burner through which, typically, a flame extends above a fixed bed of particulate steam reforming catalyst. In autothermal reforming, the heat for the endothermic steam reforming reactions is therefore provided by combustion of a portion of the hydrocarbon and any hydrogen present in the feed gas. The hydrocarbon feedstock or pre-reformed gas is typically fed to the top of the reformer and the oxygen-containing gas fed to the burner, mixing and combustion occur downstream of the burner generating a heated gas mixture which is brought to equilibrium as it passes through the steam reforming catalyst. Whereas some steam may be added to the oxygen containing gas, preferably no steam is added so that the low overall steam ratio for the reforming process is achieved. The autothermal reforming catalyst is usually nickel supported on a refractory support such as rings or pellets of calcium aluminate cement, magnesium aluminate, alpha-alumina, titanium dioxide, zirconium dioxide and mixtures thereof. In a preferred embodiment, the autothermal reforming catalyst comprises a layer of a higher activity supported Rh catalyst such as Rh on alpha-alumina or Rh on stabilised zirconia over a conventional Ni on alumina catalyst to reduce catalyst support volatilisation.

The oxygen-containing gas fed to the autothermal reformer is preferably >95% vol. $O_2$, which may be provided by an air separation unit (ASU) or from another oxygen source.

The amount of oxygen-containing gas required in the autothermal reformer is determined by the desired composition of the product gas. In general, increasing the amount of oxygen, thereby increasing the temperature of the synthesis gas leaving the autothermal reformer, causes the $[H_2]/[CO]$ ratio to decrease and the proportion of carbon dioxide to decrease.

The amount of oxygen-containing gas added is preferably such that 50 to 70 moles of oxygen are added per 100 gram atoms of carbon contained in the feed to pre-reforming and autothermal reforming stages. Preferably the amount of oxygen added is such that the synthesis gas leaves the autothermal reforming catalyst at a temperature in the range 750-1100° C. For a given feedstock/steam mixture, amount and composition of the oxygen-containing gas and reforming pressure, this temperature largely determines the composition of the synthesis gas. The amount of methane is influenced by the ATR exit temperature. High exit temperatures lower the methane content of the synthesis gas but also reduce the R-value.

The gas recovered from the synthesis gas generation unit is a synthesis gas comprising hydrogen, carbon monoxide, carbon dioxide, methane, and steam. Synthesis gas produced by an autothermal reformer may contain 2.5 to 7% by volume of carbon dioxide on a wet basis, preferably 3 to 5% by volume of carbon dioxide on a wet basis. On a dry-gas basis, i.e. without the steam, the carbon dioxide content may be in the range 2.8 to 13% by volume, preferably 4 to 8% by volume.

After leaving the autothermal reformer, the synthesis gas is then cooled in one or more steps of heat exchange, generally including at least a first stage of steam raising. Preferably, following such steam raising the synthesis gas is cooled by heat exchange with one or more of the following streams; the hydrocarbon feedstock, water (including process condensate), used to generate steam, which may be used for heating or used in the pre-reforming stage, the mixture hydrocarbon and steam, the pre-reformed gas mixture, and in the distillation of crude methanol. For safety reasons the synthesis gas is preferably not used to heat the oxygen-containing gas fed to the autothermal reformer.

The cooling is performed to lower the temperature of the synthesis gas to below the dew point such that steam condenses. The liquid process condensate may be separated from the synthesis gas, which may be termed make-up gas at this point, by conventional gas-liquid separation equipment.

The process includes a step of cooling and condensate recovery followed by a step of water or steam addition, which may appear counter intuitive. However, we have found that attempting to adjust the steam content of the synthesis gas at normal operating pressures for the process presents significant technical challenges that would be expensive to overcome. For example, operation at 30 bar abs, the water content in the make-up gas ranges from 0.25 to 3.44 mole % over the temperature range of 40 to 100° C. At 40 bar abs over the same temperature range, the water content varies from 0.19 to 2.66 mole %.

The make-up gas comprises hydrogen, carbon monoxide, carbon dioxide, and small amounts of unreacted methane, argon and nitrogen. A small amount of residual steam may also be present. The make-up gas has an R value in the range 1.70 to 1.94. The R value of the feed gas after addition of the hydrogen-rich gas, excluding any recycle gas stream, is preferably in the optimal range for methanol synthesis of from 1.95 to 2.05. Where a recycle or loop gas stream is added to the mixture of make-up gas and hydrogen-rich gas, the R value will be higher than 2.05 because the addition of water or steam to the feed gas causes an increase in the carbon dioxide removed as dissolved gas in the liquid crude methanol.

If desired, a portion of the make-up gas may be exported to external processes.

The make-up gas may be compressed in a synthesis gas compressor to the desired pressure before feeding the make-up gas to the methanol synthesis unit. A hydrogen-rich gas recovered from the purge gas is added to the make-up gas. The hydrogen-rich gas may be added to the make-up gas before or after compression in the synthesis gas compressor.

The feed gas to the methanol synthesis unit, prior to water or steam addition, may consist of the make-up gas and the hydrogen-rich gas, or where the first reactor in the methanol synthesis unit is operated in a loop, the feed gas to the methanol synthesis unit, prior to the water or steam addition, may consist of the make-up gas, the hydrogen-rich gas and a recycled gas stream comprising unreacted gases recovered from a first methanol synthesis reactor and/or a subsequent methanol synthesis reactor in the methanol synthesis unit.

The methanol synthesis unit suitably comprises one or more methanol synthesis reactors, for example first, second and optionally third methanol synthesis reactors, each containing a bed of methanol synthesis catalyst, arranged in series and/or parallel that each produce a product gas stream containing methanol. The methanol synthesis unit may therefore comprise one, two or more methanol synthesis reactors each containing a bed of copper methanol synthesis catalyst, and each reactor fed with a feed gas comprising hydrogen and carbon dioxide, each producing a product gas mixture containing methanol.

A crude methanol product stream is recovered from one or more of the product gas mixtures. This may be achieved by cooling the one or more product gas mixtures to below the dew point, condensing a crude methanol product, and separating the crude liquid methanol product from the unreacted gases. Separation of the crude liquid methanol product from one or more of the methanol product gas streams produces one or more unreacted gas mixtures.

The methanol synthesis unit is typically operated in a loop. Accordingly, a portion of an unreacted gas mixture is returned as a recycle or loop gas stream to one or more of the methanol synthesis reactors. Unreacted gas separated from a product gas mixture recovered from one methanol synthesis reactor may be returned to the same or a different methanol synthesis reactor. The unreacted gas mixture comprises hydrogen, carbon monoxide, and carbon dioxide and so may be used to generate additional methanol. A recycle gas stream may be recovered from at least one of one of the methanol product gas streams and recycled to at least one of the methanol synthesis reactors. If there are multiple recycle gas streams, these may be recycled separately to one or more of the methanol synthesis reactors or combined and fed to one or more of the methanol synthesis reactors.

The methanol synthesis unit may comprise a first methanol synthesis reactor and a second methanol synthesis reactor connected in series. In such an arrangement, gas fed to the second methanol synthesis reactor may comprise at least a portion of an unreacted gas mixture from the methanol product gas stream recovered from the first methanol synthesis reactor. Whereas the gas fed to the second methanol synthesis reactor may comprise of all of the unreacted gases from methanol product gas stream from the first methanol synthesis reactor, if desired a portion of the unreacted gas stream not fed to the second methanol synthesis reactor, may be recycled to the feed to the first methanol synthesis reactor. Particularly preferred methanol synthesis units are described in U.S. Pat. No. 7,790,775, WO2017/121980 and WO2017/121981.

For example, the methanol synthesis unit may comprises a first methanol synthesis reactor and a second methanol synthesis reactor connected in series, wherein the first methanol synthesis reactor operates on a once-through basis and gas fed to the second methanol synthesis reactor consists of all of an unreacted gas stream recovered from the first methanol synthesis reactor and a recycle gas stream recovered from the second methanol synthesis reactor.

Alternatively, the methanol synthesis unit may comprise a first methanol synthesis reactor and a second methanol synthesis reactor connected in series, wherein a portion of an unreacted gas stream recovered from the first methanol synthesis reactor is recycled to the first methanol synthesis reactor and a portion of an unreacted gas stream recovered from the second methanol synthesis reactor is recycled to the second methanol synthesis reactor.

Alternatively, the methanol synthesis unit may comprise a first methanol synthesis reactor and a second methanol synthesis reactor connected in series, wherein a portion of an unreacted gas stream recovered from the second methanol synthesis reactor is recycled to the first methanol synthesis reactor.

In the process, a stream of water or steam is added to the feed gas to the methanol synthesis unit. Water may be mains water or demineralised water or a water stream recovered from the process, such as a condensate, a water stream recovered by distillation of crude methanol, or a water stream recovered from a purge gas wash unit. The stream of water or steam may consist of water or steam, although small amounts of methanol or other substances may be present if the water or steam is recovered from the process. For example, the $H_2O$ content of the water or steam may be ≥90% by volume, preferably ≥95% by volume, more preferably ≥98% by volume.

Water or steam may be added to the feed gas to one or more of the methanol synthesis reactors in the methanol synthesis unit. For example, water or steam may be added to the feed gas to a methanol synthesis unit comprising a single methanol synthesis reactor operating in a loop. Alternatively, water or steam may be added to the feed gas to a methanol synthesis unit comprising two or more methanol synthesis reactors operating in series or in parallel. In the case of the methanol synthesis unit comprising two or more methanol synthesis reactors operating in series, the water or steam is preferably added to the feed gas before the first methanol synthesis reactor.

Water may be added using a vaporiser, which may comprise a vessel through which the feed gas is passed and into which liquid water is added, e.g. sprayed, causing it to be vaporised. The vessel may contain a structured packing or bed of shaped inert material, e.g. alumina pellets or extrudates, to provide a surface from which the water may be more efficiently vaporised. The water may be boiler feed water or water obtained from the process condensate. A particularly useful source of the water is water recovered from a purge gas wash column. The advantages of using this source is that this stream is already at high pressure and the small amount of contained methanol will help control reactor peak temperature by tightening approach to equilibrium.

Steam may be added to the feed gas by direct addition using known methods. The steam may be generated from boiler feed water or from process condensate recovered from the synthesis gas.

Addition of the water or steam to the feed gas may be performed before or after preheating the feed gas upstream of the methanol synthesis unit, for example, before or after preheating the feed gas in a gas-gas interchanger. Adding the water or steam before the gas-gas interchanger may provide improved mixing of the water or steam upstream of the methanol synthesis reactor.

The addition of water or steam to the feed to the methanol synthesis reactor promotes the water-gas shift reaction over the methanol synthesis catalyst, whereby carbon monoxide reacts with the water or steam to form carbon dioxide and hydrogen. Thus, the carbon dioxide to carbon monoxide ratio in the product gas mixture is increased. The amount of water or steam added to the feed gas to the methanol synthesis unit may be in the range of 0.1 to 6 mole % of the make-up gas. Adding too much water or steam can increase the R value of a feed gas containing a recycle gas stream due to removal of an excess amount of dissolved carbon dioxide in the crude methanol product. Additionally, excess hydrogen may also be rejected from the purge gas, resulting in reduced methanol production for a fixed amount of make-up gas. Too much water or steam can also reduce the methanol production due to equilibrium limitations and depression of the forward reaction rate. Conversely, adding too little water or steam can decrease the R value of a feed gas containing a recycle gas stream to below the desired minimum, which can result in an increase in unwanted by-products.

Where the methanol synthesis unit comprises a single methanol synthesis reactor, the reactor may be an un-cooled adiabatic reactor. Alternatively, the reactor may be cooled by heat exchange with a methanol synthesis feed gas, such as in a quench reactor, a tube-cooled converter or a gas-cooled converter. Alternatively, the methanol synthesis reactor may be cooled by boiling water under pressure, such as in an axial-flow steam-raising converter or a radial-flow steam-raising converter. Where the methanol synthesis unit comprises two or more methanol synthesis reactors, they may comprise any combination of these, although combinations of axial-flow or radial-flow steam raising converters and tube-cooled or gas-cooled converters, or, combinations of axial-flow steam-raising converters, followed by radial-flow steam raising converters are preferred.

In an adiabatic reactor, the methanol synthesis feed gas may pass axially, radially, or axially and radially through a fixed bed of particulate methanol synthesis catalyst. The exothermic methanol synthesis reactions occur resulting in an increase in the temperature of the reacting gases. The inlet temperature to the bed therefore is desirably cooler than in cooled reactor systems to avoid over-heating of the catalyst which can be detrimental to selectivity and catalyst life. Alternatively, a cooled reactor may be used in which heat exchange with a coolant within the reactor may be used to minimise or control the temperature. A number of cooled reactor types exist that may be used. In one configuration, a fixed bed of particulate catalyst is cooled by tubes or plates through which a coolant heat exchange medium passes. In another configuration, the catalyst is disposed in tubes around which the coolant heat exchange medium passes. The methanol synthesis reactors may be cooled by the feed gas or by boiling water, typically under pressure. For example, the methanol synthesis reactor may be an axial-flow steam-raising converter, a radial-flow steam raising converter, a gas-cooled converter, or a tube cooled converter.

In an axial-flow, steam-raising converter (aSRC), the methanol synthesis feed gas typically passes axially through vertical, catalyst-containing tubes that are cooled in heat exchange with boiling water under pressure flowing outside the tubes. The catalyst may be provided in pelleted form directly in the tubes or may be provided in one or more cylindrical containers that direct the flow of synthesis gas both radially and axially to enhance heat transfer. Such contained catalysts and their use in methanol synthesis are described in U.S. Pat. No. 8,785,506. Steam raising converters in which the catalyst is present in tubes cooled by boiling water under pressure offer a particularly useful means to remove heat from the catalyst.

In a radial-flow steam raising converter (rSRC) the methanol synthesis feed gas typically passes radially (inwards or outwards) through a bed of particulate catalyst which is cooled by a plurality of tubes or plates through boiling water under pressure is fed as coolant. Such reactors are known and are described for example in U.S. Pat. No. 4,321,234. They offer a lower pressure drop than an aSRC but have a more complicated internal construction.

In a tube-cooled converter, the catalyst bed is cooled by methanol synthesis feed gas passing through tubes disposed within the bed that are open-ended and discharge the heated gas to the space above the catalyst within the reactor shell. The heated gas may then pass directly through the bed of catalyst without leaving the converter. TCC's can provide sufficient cooling area for a range of synthesis gas compositions and may be used under a wide range of conditions. As an alternative to a TCC, a gas-cooled converter (GCC) may be used to cool the catalyst bed by passing the methanol synthesis feed gas though tubes or plates in a heat exchanger-type arrangement. In this case the heated synthesis gas is withdrawn from the converter before being returned back to the catalyst bed. An example of a GCC is described in U.S. Pat. No. 5,827,901.

Alternatively, the methanol synthesis reactor may be a quench reactor in which one or more fixed beds of particulate methanol synthesis catalyst are cooled by a methanol synthesis feed gas mixture injected into the reactor within or between the beds. Such reactors are described, for example, in U.S. Pat. No. 4,411,877.

In a process comprising first and second methanol synthesis reactors, the first methanol synthesis reactor is preferably cooled by boiling water, such as in an axial-flow steam-raising converter or a radial-flow steam-raising converter, more preferably an axial-flow steam raising converter. The second methanol synthesis reactor may be a radial-flow steam-raising converter. Such arrangements are particularly useful in the present invention due to the characteristics and performance of these reactors with different feed gas mixtures. Alternatively, the second methanol synthesis reactor may be a gas-cooled converter or tube-cooled converter.

The methanol synthesis catalysts are suitably copper-containing methanol synthesis catalysts, which are commercially available. In particular, suitable methanol synthesis catalysts are particulate copper/zinc oxide/alumina catalysts, which may comprise one or more promoters. The methanol synthesis catalysts in each of the methanol synthesis reactors may be the same or different. For example, a methanol synthesis catalyst in the methanol synthesis reactor to which the water- or steam-containing feed gas is fed, may have a composition that is resistant to water or steam and favours the water-gas shift reaction. The copper oxide content of the catalyst (expressed as CuO) may be in the range of 30 to 70% by weight. Within this range a copper oxide content in the range of 50 to 70% by weight, preferably 60 to 70% by weight, is of general application for methanol synthesis, whereas for the water-gas shift reaction, the copper oxide content may be generally lower, for example in the range of 30 to 60% by weight. The weight ratio of Cu:Zn (expressed as CuO:ZnO) may be 1:1 or higher but is preferably in the range of 2:1 to 3.5:1, especially 2.5:1 to 2.75:1 for methanol synthesis catalysts and in the range of 1.4:1 to 2.0:1 for water-gas shift catalysts. In the methanol synthesis catalysts, the catalyst preferably contains 20-30% by weight zinc oxide. The catalyst typically contains alumina, which may be in an amount in the range 5 to 20% by weight. Particularly suitable catalysts are silica-doped methanol synthesis catalysts as described in WO2020212681 (A1), which are surprisingly stable to feed gases containing water or steam.

Methanol synthesis may be performed in the methanol synthesis reactors at pressures in the range 10 to 120 bar abs, and temperatures in the range 130° C. to 350° C. The pressure at the reactor inlets is preferably 50-100 bar abs, more preferably 70-90 bar abs. The temperature of the synthesis gas at the reactor inlets is preferably in the range 200-250° C. and at the outlets preferably in the range 230-280° C. Each methanol synthesis reactor produces a product gas mixture. In the current process a liquid methanol-containing stream is preferably recovered from each product gas mixture before it is further used. This may be achieved by cooling the one or more product gas mixtures to below the dew point, condensing a crude methanol product, and separating the crude liquid methanol product from the unreacted gases. Conventional heat exchange and gas-liquid separation equipment may be used. A particularly suitable heat exchange apparatus includes a gas-gas interchanger that uses a feed gas mixture for a methanol synthesis reactor to cool a methanol product gas stream from that reactor. Using a gas-gas interchanger usefully allows improved control of steam generation in steam-raising converters. Where there are two or more methanol synthesis reactors, the product gas mixtures may be separately cooled or combined and cooled together to produce the crude methanol stream. The cooling of the product gas mixture is preferably performed to 50° C. or less, preferably 45° C. or less, such that the capture of dissolved carbon dioxide in the crude methanol product is maximised. However, cooling to below about 40° C. is not necessary.

The liquid crude methanol recovered from the one or more product gas mixtures contains dissolved carbon dioxide and therefore is preferably treated by first reducing its pressure/and or increasing its temperature and separating vapourised carbon dioxide using a flash-gas vessel.

The process may include a step of recovering a carbon dioxide stream from the crude methanol. The recovered carbon dioxide stream is not recycled to the process but may, after optional purification, be used in external chemical synthesis processes, may be used for enhanced oil recovery, or may be sequestered in a carbon capture and storage unit. The carbon dioxide stream may be useful as a chemical feedstock, for example for the manufacture of acetic acid, or in the manufacture of urea in an integrated ammonia-methanol-urea coproduction process.

The carbon dioxide-depleted crude methanol may then be treated conventionally by distillation to produce a purified methanol product. If desired, a portion of the carbon-dioxide depleted crude methanol product may usefully be recirculated as a wash stream to the gas-liquid separator to enhance the capture of carbon dioxide in the crude methanol product.

The portion of the unreacted gas mixture making up the gas stream recycled to the loop is compressed by one or more compressors or circulators. The compression may take place before the stream is divided, e.g. to provide a purge gas stream, or after it is divided, or after combination of the recycle gas stream with the feed gas. The recycle ratios to form the feed gas mixtures to the one or more methanol synthesis reactors may be in the range 0.5:1 or lower, to 5:1, preferably 1:1 to 3:1. By the term "recycle ratio", we mean the molar flow ratio of the recycled unreacted gas stream to the make-up gas that forms the gas mixture fed to the methanol synthesis reactor.

A portion of the unreacted gas mixture separated from the crude liquid methanol is removed from the loop or recycle stream as the purge gas stream, which is used to prevent the build-up of unwanted inerts in the process. The purge gas stream may be removed continuously or periodically. The purge gas stream may be recovered from the separated unreacted gases before or after compression in the circulator. A purge gas recovered downstream of compressor can give more driving force and aid membrane separation.

In the process, at least a portion of the purge gas stream is separated into a hydrogen-rich gas stream, which is recycled to the make-up gas for the process. This will result in a carbon-rich off gas stream. By "carbon-rich off gas stream" we mean a gas stream that has a higher proportion of carbon containing compounds (carbon monoxide, carbon dioxide and methane) than the purge gas. While individual components may have the same, or even lower, proportion than in the purge gas, the total of all carbon-containing components will be in a higher proportion in the carbon-rich gas compared to the purge gas. Preferably all of the purge gas stream is subjected to a separation step. The separation of the hydrogen-rich and carbon-rich gas streams may be practiced using known separation equipment such as hydrogen membrane separator or a pressure swing adsorption unit, a cold box separation system or any combination of these. Using these techniques over 50% of the hydrogen present in the purge gas stream may be recovered.

It will be understood that by adding the hydrogen-rich gas stream to the make-up gas, that the stoichiometry value R of the feed gas will be increased. If desired additional hydrogen from an external source may also be added.

In the present process, the carbon rich off-gas, which contains inerts, is desirably sent as fuel, e.g. to a fired heater, such as a fired heater used to superheat steam, or preheat and/or reheat the feeds in the synthesis gas generation unit. Alternatively, the carbon rich off gas may be exported from the process for use as a fuel.

The hydrogen-rich gas recovered from the purge gas stream desirably comprises >80% by volume of $H_2$. The separated hydrogen, in addition to being recycled to the methanol loop may also be used upstream in hydrodesulphurisation of the hydrocarbon feedstock and/or exported from the process for other use. However, in a preferred embodiment, most, e.g. at least 51% by volume, of the separated hydrogen is fed to the methanol synthesis loop.

The carbon-rich gas, which will typically contain carbon oxides and methane, may be used as fuel, e.g. in a fired heater. The carbon rich-gas may usefully be used as a fuel for a fired heater used to heat process feeds such as the pre-reformer and autothermal reformer feed streams.

A $CO_2$ removal unit may optionally be included to recover carbon dioxide from the unreacted gas recovered from the product gas mixture, e.g. before the unreacted gas is recycled or fed to one or more further methanol synthesis reactors in the methanol synthesis unit. Where a $CO_2$ removal unit is employed, the resulting product gas stream depleted in carbon dioxide, may be returned to form part of the feed gas. The $CO_2$ removal unit may be any conventional $CO_2$ removal unit that operates by physical absorption, chemical absorption, adsorption into a porous material, or uses a membrane to selectively separate $CO_2$ from the carbon-rich stream, thereby forming a methane-rich stream. A membrane $CO_2$-removal unit is preferred. The recovered $CO_2$ stream may contain small amounts of methane and inerts and so may be used as a fuel, e.g. in a fired heater. Alternatively, the recovered $CO_2$ stream, optionally after further purification, may be fed to an external chemical synthesis process, used for enhanced oil recovery or sequestered.

The purge gas stream mixture may contain methanol and so, if desired, upstream of the separation of the hydrogen-rich gas and the carbon-rich gas, methanol may be recovered from the purge gas stream using a water wash. Preferably at least a portion of the resulting wash water containing methanol is added to the feed gas fed to methanol synthesis unit. Any purge gas wash water containing methanol not added to the feed gas to the methanol synthesis unit may be sent for purification with the crude methanol.

The crude methanol stream recovered from the methanol production unit contains water, along with small amounts of higher alcohols and other impurities. The crude methanol may first be fed to a flash vessel or column where dissolved gases are released and separated from the crude liquid methanol stream. The crude liquid methanol may also be subjected to one or more purification stages including one or more, preferably two or three, stages of distillation in a methanol purification unit comprising one, two or more distillation columns. The de-gassing stage and distillation stages may be heated using heat recovered from the process, for example in the cooling of a product gas stream, a synthesis gas stream or other sources. Typically, at least a portion of the crude methanol is purified by distillation to produce a purified methanol product.

The purified methanol product may be subjected to further processing, for example to produce derivatives such as dimethyl ether or formaldehyde. Alternatively, the methanol may be used as a fuel.

Figure 2:
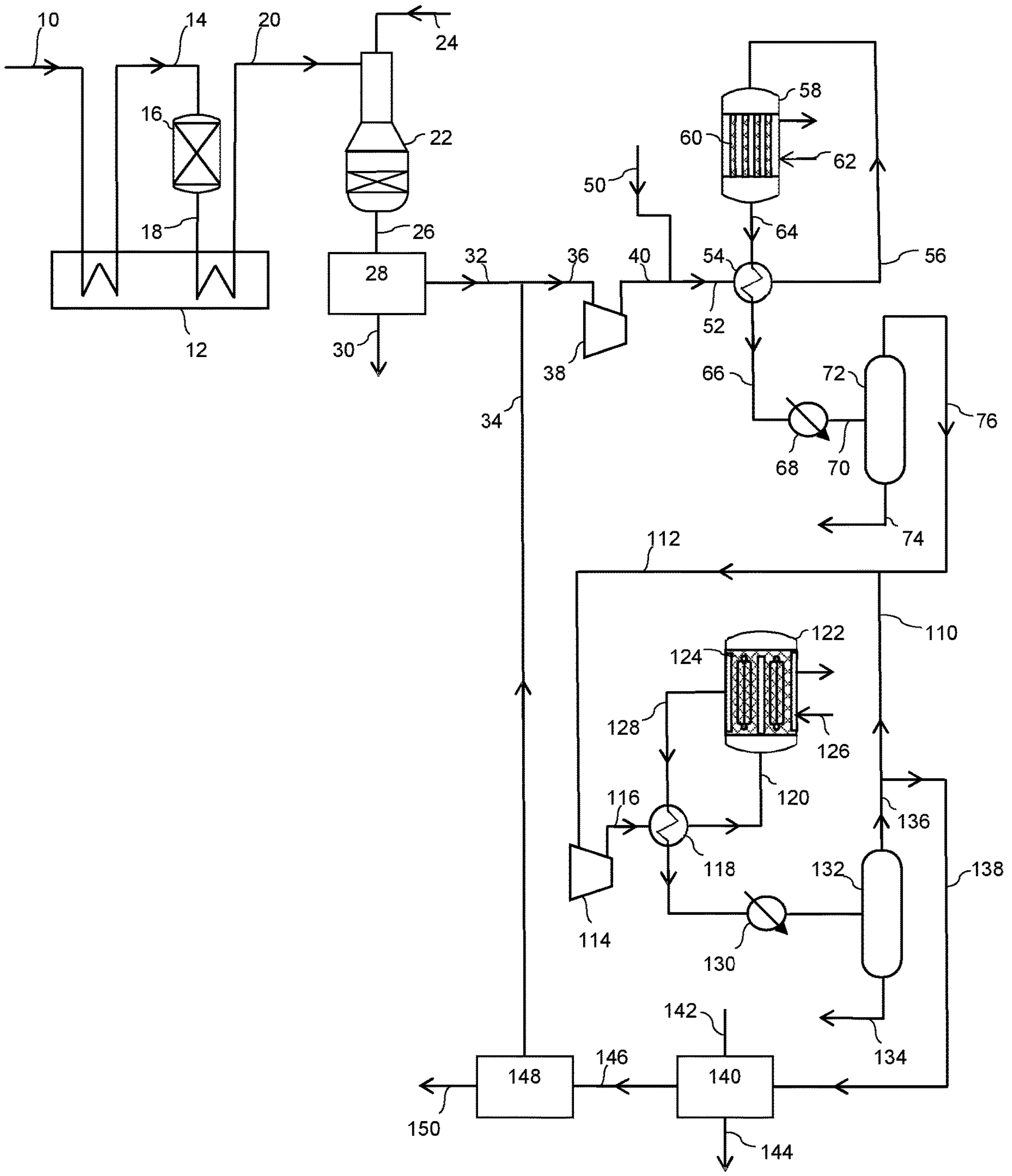
FIG. 2 depicts a further process according to another embodiment of the invention.
Figure 3:
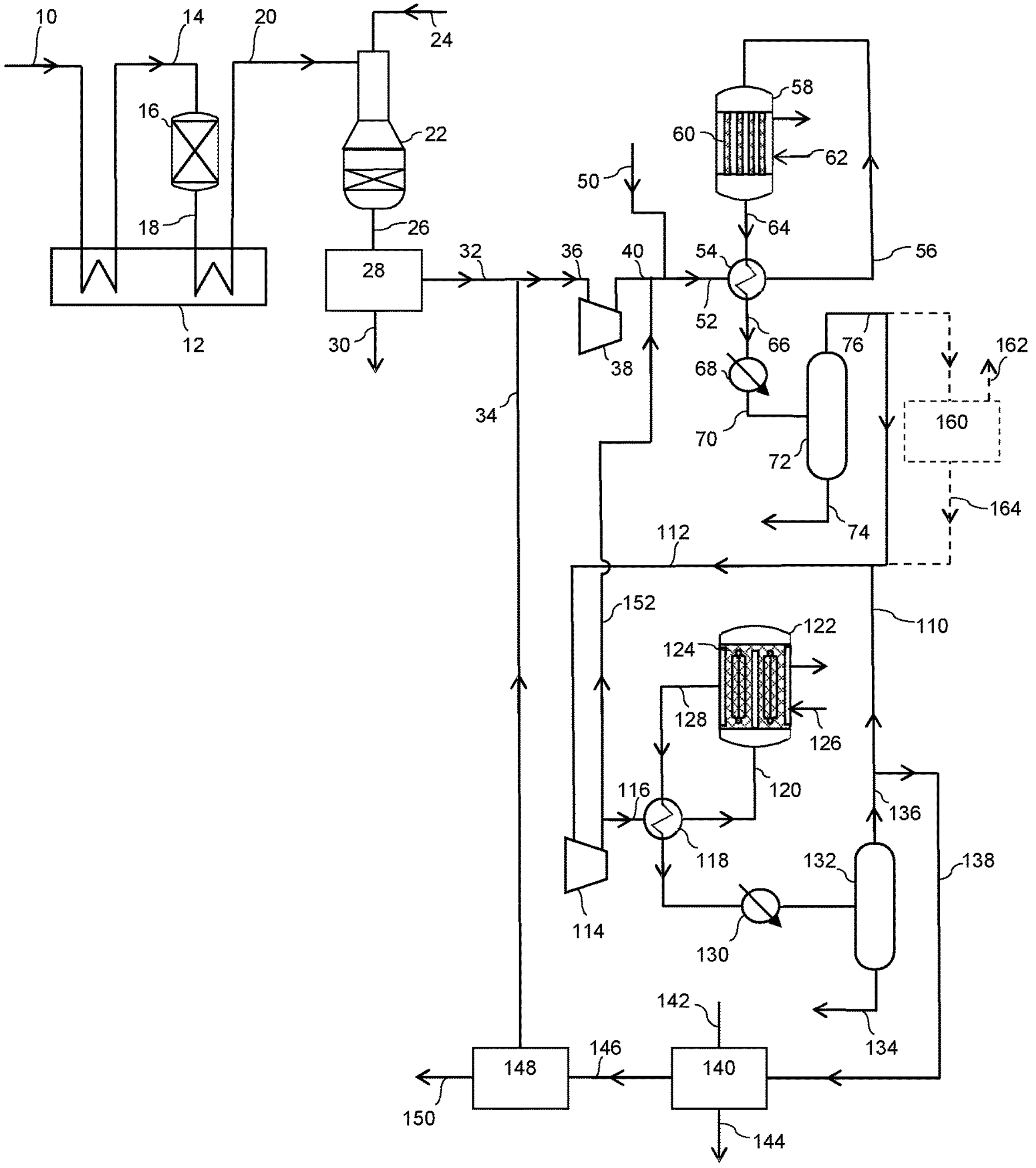
FIG. 3 depicts a further process according to another embodiment of the invention.
Figure 4:
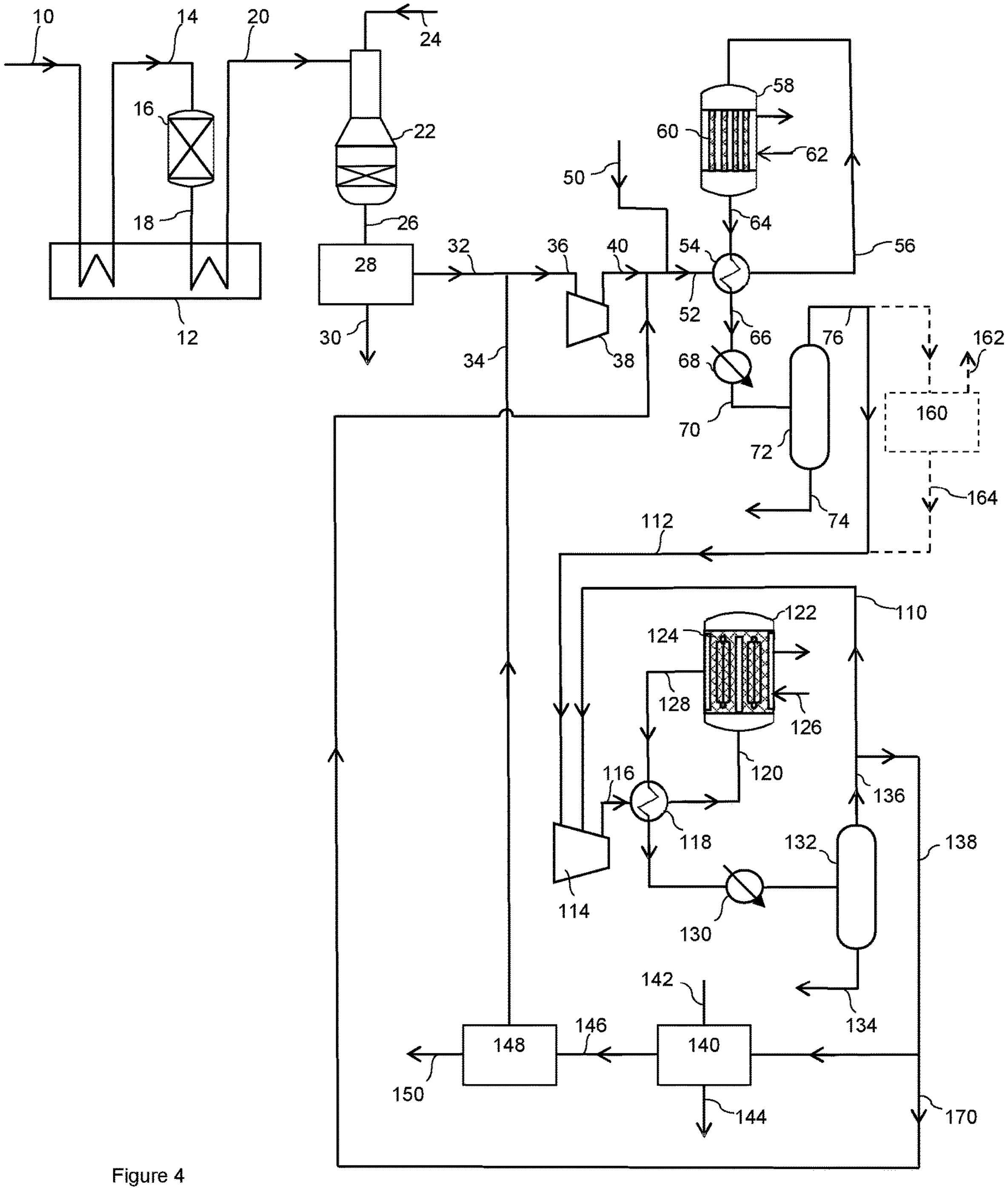
FIG. 4 depicts a further process according to another embodiment of the invention.

In FIGS. 1 to 4, the synthesis gas generation unit comprises a pre-reformer and an autothermal reformer. In FIGS. 1, the methanol synthesis unit comprises a single stage, i.e. one methanol synthesis converter, or parallel converters of the same design, operated in a loop. In FIGS. 2 and 3, the methanol synthesis unit comprises two stages connected in series, with the first stage operated on a once-through basis and the second stage operated in a loop. In FIG. 4, the methanol synthesis unit comprises two methanol stages connected in series, with the both stages operated in loops.

It will be understood by those skilled in the art that the drawings are diagrammatic and that further items of equipment such as feedstock drums, pumps, vacuum pumps, compressors, gas recycling compressors, temperature sensors, pressure sensors, pressure relief valves, control valves, flow controllers, level controllers, holding tanks, storage tanks and the like may be required in a commercial plant. Provision of such ancillary equipment forms no part of the present invention and is in accordance with conventional chemical engineering practice.

In FIG. 1, a mixture of natural gas and steam supplied by line 10 is fed to a fired heater 12 where it is heated. The heated gas mixture is fed from the fired heater 12 by line 14 to a pre-reformer 16 containing a fixed bed of particulate steam reforming catalyst. The heated gas mixture is reformed adiabatically over the catalyst thereby converting higher hydrocarbons present in the natural gas to methane, carbon oxides and hydrogen. The pre-reformed gas mixture is fed from the pre-reformer 16 by line 18 to the fired heater 12 where it is heated to the autothermal reformer inlet temperature. The re-heated pre-reformed gas mixture is fed from the fired heater 12 via line 20 to an autothermal reformer 22 fed with an oxygen stream 24. In the autothermal reformer, the pre-reformed gas mixture is partially combusted with the oxygen in a burner mounted near the top and the resulting hot, partially-combusted gas brought to equilibrium through a bed of steam reforming catalyst disposed beneath the burner. The resulting autothermally reformed synthesis gas stream is fed from the autothermal reformer 22 via line 26 to a heat recovery unit 28 comprising one or more heat exchangers, where it is cooled to below the dew point to condense steam. Process condensate 30 is removed from the cooled gas mixture using gas-liquid separation equipment in the heat recovery unit to produce a make-up gas. A portion of the condensate 30 may be used to generate the steam used to prepare the feed gas 14 provided to the pre-reformer 16. The make-up gas is recovered from the heat recovery unit 28 via line 32, combined with a hydrogen-rich stream provided via line 34, and the resulting mixture fed via line 36 to a syngas compressor 38 where it is compressed. A compressed gas mixture is recovered from the syngas compressor 38 via line 40 and combined with a recycle loop gas provided by line 42 to form a feed gas mixture, which is fed via line 44 to a circulating compressor 46, where the mixture is compressed to the loop pressure. A compressed feed gas is recovered from the circulating compressor 46 via line 48 and mixed with a stream of steam fed via steam injection line 50. The resulting mixture of feed gas and steam is fed via line 52 to a gas-gas interchanger 54, where it is heated to the methanol converter inlet temperature and then fed via line 56 to the inlet of a methanol synthesis reactor 58. Whereas a single converter is depicted, it will be understood that this flowsheet may operate with two or more converters operated in parallel. The methanol synthesis reactor 58 is an axial-flow steam-raising converter comprising methanol synthesis catalyst-filled tubes 60 cooled by boiling water under pressure 62. Methanol synthesis and water-gas shift reactions take place in the reactor 58 to generate a product gas mixture comprising methanol, unreacted hydrogen, and carbon dioxide. The product gas mixture is recovered from the reactor 58 via line 64, cooled in the interchanger 54 and fed via line 66 to one or more further heat exchangers 68 where it is cooled to below the dew point to condense a liquid crude methanol. The cooled mixture is passed from the one or more heat exchangers 68 via line 70 to a gas liquid separator 72, where the unreacted gases are separated from the liquid crude methanol, which is recovered from the separator 72 via line 74. The crude methanol is sent to a distillation and purification unit (not shown) where it is degassed and distilled in two or three stages of distillation to produce a purified methanol product. The unreacted gases are recovered from the separator 72 and divided. A portion is passed via line 42 as the recycle loop gas to form part of the feed gas to the methanol synthesis reactor 58. The remaining portion is fed via line 78 as a purge gas, to a purge gas washing unit 80, which is fed with a water stream 82, and which generates a purge gas wash stream 84 containing a small amount of methanol. The purge gas wash stream is heated to generate steam, a portion of which may be fed to the feed gas mixture via line 50. A washed purge gas is recovered from the purge gas washing unit 80 and fed via line 86 to a membrane hydrogen recovery unit 88, where a hydrogen-rich stream is separated from the washed purge gas and supplied via line 34 to the make-up gas stream in line 32. A carbon rich off gas is recovered from the hydrogen recovery unit 88 via line 90 and sent as fuel to be combusted in the fired heater 12.

In FIG. 2, the synthesis gas generation unit is the same as depicted in FIG. 1. However, whereas in FIG. 1, the methanol synthesis unit operates a single reactor in a loop, the methanol synthesis unit in FIG. 2 operates with two methanol synthesis reactors connected in series, with a first reactor operating on a once-through basis, and the unreacted gases from the separator downstream of the first reactor fed instead to a further methanol synthesis reactor operating in a loop. Thus, in FIG. 2, the compressed mixture of make-up gas and hydrogen-rich gas in line 40 is mixed with steam in line 50, heated in gas-gas interchanger 54, passed through reactor 58, cooled in the interchanger 54 and further heat exchangers 68 and passed to the gas-liquid separator 72, from which a first stream of crude liquid methanol 74 is recovered. A first unreacted gas mixture 76 recovered from the gas-liquid separator 72 is combined with a second unreacted gas mixture from line 110 and the combined feed gas passed via line 112 to circulating compressor 114. The compressed feed gas is fed from the compressor 114 via line 116 to a second gas-gas interchanger 118 where it is heated and then fed via line 120 to the inlet of a radial-flow steam-raising converter 122 containing an annular bed of catalyst 124 cooled by tubes or plates containing boiling water under pressure 126. Whereas a radial flow steam-raising converter is depicted, the process may equally be performed using an axial-flow steam-raising converter, a gas-cooled converter, or a tube-cooled converter. A second product gas mixture is recovered from the reactor 122 via line 128 and cooled in the interchanger 118 and one or more further heat exchangers 130 to below the dew point. The cooled mixture is then passed from the heat exchangers 130 to a second gas-liquid separator 132, from which a second stream of liquid crude methanol is recovered via line 134. The first and second crude liquid methanol streams may, if desired, be combined before being sent for purification to produce a purified methanol product as described above. An unreacted gas mixture 136 is recovered from the second gas-liquid separator 132 and divided into the second unreacted gas stream 110 and a purge stream 138. The purge 138 is fed to a purge gas washing unit 140, which is fed with a water stream 142, and which generates a purge gas wash stream 144 containing a small amount of methanol. The purge gas wash stream is heated to generate steam, a portion of which may be fed to the feed gas mixture via line 50. A washed purge gas is recovered from the purge gas washing unit 140 and fed via line 146 to a membrane hydrogen recovery unit 148, where a hydrogen-rich stream is separated from the washed purge gas and supplied via line 34 to the make-up gas stream in line 32. A carbon rich off gas is recovered from the hydrogen recovery unit 148 via line 150 and sent as fuel to be combusted in the fired heater 12.

In FIG. 3, the synthesis gas generation unit and methanol synthesis unit are the same as depicted in FIG. 2, except that a portion of the gas fed to the radial-flow steam-raising converter is recycled to supplement the feed gas to the axial-flow steam-raising converter. Thus, the feed gas 116 to the radial-flow steam-raising converter 122, is divided into first and second portions. The first portion is heated in interchanger 118 and fed to the radial-flow steam-raising converter 122. The second portion is fed via line 152 to the compressed feed gas in line 40 upstream of the steam or water addition via line 50, heated in interchanger 54 and fed to the axial-flow steam-raising converter 58.

Optionally, as shown in dashed lines, at least a portion of the unreacted gas mixture 76 recovered from the first gas-liquid separator 72 may be passed to a $CO_2$ removal unit 160 to remove a portion of the carbon dioxide from the first unreacted gas mixture. The $CO_2$ removal unit 160 may suitably be a membrane unit that produces a $CO_2$-depleted gas mixture 164 that is combined with the second unreacted gas mixture 110 to form the feed gas for the radial-flow steam-raising converter. The $CO_2$ removal unit also produces a $CO_2$ stream 162, which may be fed to an external process or sequestered in a $CO_2$-capture facility.

FIG. 4, the synthesis gas generation unit and methanol synthesis unit are the same as depicted in FIG. 2, except that the purge gas mixture 138 taken from the unreacted gas mixture 136 is divided. A first portion is passed to the purge gas washing unit 140 and hydrogen separation unit 148 for generation of the hydrogen-rich stream 34. A second portion bypasses these and is recycled to the compressed feed gas in line 40 upstream of the steam addition via line 50 to the feed gas for the axial-flow steam-raising converter 58. In this arrangement, the second unreacted gas stream 110 is not combined with the unreacted gas stream in line 76 (or optionally the $CO_2$-depleted gas stream 164) but is instead fed directly to the circulating compressor 114. Optionally, as shown in FIG. 3, at least a portion of the unreacted gas mixture 76 recovered from the first gas-liquid separator 72 may be passed to a $CO_2$ removal unit 160 to remove a portion of the carbon dioxide from the first unreacted gas mixture, thereby generating a $CO_2$ stream 162 and a $CO_2$-depleted gas 164, which may be fed to the circulating compressor 114.

The invention will be further described by reference to the following calculated examples prepared using conventional modelling software suitable for methanol processes. These examples are all based on same quantity of $H_2$+CO in $Nm^3/h$ at the exit of the ATR, which was operated at a steam to carbon ratio of 0.6:1 and a pressure of 34 bara.

Example 1

Example 1 is an example of a flowsheet in accordance with FIG. 1. The process conditions and compositions of the various streams are set out below.

| Stream number | 20 | 24 | 26 | 30 | 32 | 34 | 36 |
|---|---|---|---|---|---|---|---|
| Temperature (° C.) | 650 | 228 | 1050 | 92 | 45 | 55 | 46 |
| Pressure (bar a) | 35.4 | 39.5 | 34.0 | 30.9 | 30.9 | 30.9 | 30.9 |
| Mass flow (tonne/h) | 201.1 | 126.0 | 327.1 | 76.2 | 250.8 | 21.7 | 272.5 |
| Molar flow (kgmole/h) | 11972 | 3960 | 25666 | 4230 | 21436 | 2789 | 24225 |
| Molecular weight | 16.79 | 31.83 | 12.74 | 18.02 | 11.70 | 7.77 | 11.25 |
| Composition (kgmole/h) | | | | | | | |
| Water | 3986.6 | 55.5 | 4305.8 | 4228.2 | 77.4 | 9.5 | 86.9 |
| Hydrogen | 486.0 | — | 13849.3 | — | 13849.3 | 2339.5 | 16188.8 |
| Carbon monoxide | 3.9 | — | 6110.3 | 0.7 | 6109.6 | 50.4 | 6160.1 |
| Carbon dioxide | 267.5 | — | 974.7 | 0.9 | 973.8 | 318.7 | 1292.5 |
| Nitrogen | 35.9 | — | 35.9 | — | 35.9 | 7.3 | 43.3 |
| Argon | — | 11.7 | 11.7 | — | 11.7 | 5.5 | 17.2 |
| Methane | 7192.2 | — | 378.3 | — | 378.2 | 58.0 | 436.2 |
| Methanol | — | — | — | — | — | — | — |
| Oxygen | — | 3892.7 | — | — | — | — | — |
| Lights | — | — | — | — | — | — | — |
| Heavies | — | — | — | — | — | — | — |

| Stream number | 42 | 44 | 50 | 56 | 64 | 70 | 74 |
|---|---|---|---|---|---|---|---|
| Temperature (° C.) | 45 | 88 | 303 | 230 | 251 | 45 | 45 |
| Pressure (bar a) | 76.8 | 76.3 | 84.2 | 83.0 | 80.0 | 77.1 | 77.0 |
| Mass flow (tonne/h) | 462.1 | 734.7 | 9.9 | 744.6 | 744.6 | 744.6 | 239.8 |
| Molar flow (kgmole/h) | 42872 | 67097 | 550 | 67647 | 54761 | 54761 | 7936 |
| Molecular weight | 10.78 | 10.95 | 18.02 | 11.01 | 13.60 | 13.60 | 30.22 |
| Composition (kgmole/h) | | | | | | | |
| Water | 21.7 | 108.6 | 550.0 | 658.6 | 1195.5 | 1195.5 | 1171.9 |
| Hydrogen | 29846.5 | 46035.3 | — | 46035.3 | 32622.9 | 32622.9 | 24.1 |
| Carbon monoxide | 2542.3 | 8702.3 | — | 8702.4 | 2788.6 | 2788.6 | 12.0 |
| Carbon dioxide | 5303.4 | 6595.8 | — | 6595.8 | 6063.8 | 6063.8 | 271.5 |
| Nitrogen | 453.4 | 496.7 | — | 496.7 | 496.6 | 496.6 | 1.5 |
| Argon | 177.6 | 194.8 | — | 194.8 | 194.8 | 194.8 | 0.9 |
| Methane | 4249.3 | 4685.5 | — | 4685.5 | 4685.5 | 4685.5 | 44.4 |
| Methanol | 272.8 | 272.8 | — | 272.8 | 6698.9 | 6698.9 | 6401.2 |

-continued

| Stream number | 42 | 44 | 50 | 56 | 64 | 70 | 74 |
|---|---|---|---|---|---|---|---|
| Oxygen | — | — | — | — | — | — | — |
| Lights | 5.1 | 5.0 | — | 5.1 | 12.1 | 12.1 | 6.5 |
| Heavies | — | — | — | — | 2.1 | 2.1 | 2.1 |

| Stream number | 76 | 78 | 82 | 84 | 86 | 90 |
|---|---|---|---|---|---|---|
| Temperature (° C.) | 45 | 45 | 46 | 51 | 53 | 54 |
| Pressure (bar a) | 77.0 | 76.2 | 76.5 | 76.2 | 75.8 | 72.6 |
| Mass flow (tonne/h) | 504.7 | 42.6 | 7.0 | 7.7 | 41.9 | 20.2 |
| Molar flow (kgmole/h) | 46825 | 3953 | 390 | 408 | 3935 | 1146 |
| Molecular weight | 10.78 | 10.78 | 18.02 | 18.96 | 10.65 | 17.64 |
| Composition (kgmole/h) | | | | | | |
| Water | 23.7 | 2.0 | 390.0 | 381.5 | 10.4 | 0.9 |
| Hydrogen | 32598.6 | 2752.0 | — | — | 2752.1 | 412.7 |
| Carbon monoxide | 2776.7 | 234.4 | — | 0.0 | 234.4 | 183.9 |
| Carbon dioxide | 5792.3 | 489.0 | — | 1.3 | 487.7 | 169.0 |
| Nitrogen | 495.2 | 41.8 | — | — | 41.8 | 34.5 |
| Argon | 193.9 | 16.4 | — | — | 16.4 | 10.9 |
| Methane | 4641.1 | 391.8 | — | 0.1 | 391.7 | 333.6 |
| Methanol | 298.0 | 25.2 | — | 25.0 | — | 0.1 |
| Oxygen | — | — | — | — | — | — |
| Lights | 5.5 | 0.5 | — | — | 0.5 | 0.5 |
| Heavies | — | — | — | — | — | — |

Example 2—Comparative

Example 2 is the same as Example 1, and is based on the process depicted in FIG. 1 but omits the steam injection line 50 and adds a make-up gas feed line, which passes a portion of the make-up gas, identified below as line 41, from the compressed make-up gas mixture line to the washed purge gas 86, which is fed to the hydrogen recovery unit 88. This is an example of a process claimed in WO2016180812 A1. The process conditions and compositions of the various streams are set out below.

| Stream number | 20 | 24 | 26 | 30 | 32 | 34 | 36 |
|---|---|---|---|---|---|---|---|
| Temperature (° C.) | 650 | 228 | 1050 | 93 | 45 | 101 | 51 |
| Pressure (bar a) | 35.4 | 39.5 | 34.0 | 30.9 | 30.9 | 30.9 | 30.9 |
| Mass flow (tonne/h) | 201.1 | 126.0 | 327.1 | 76.2 | 250.8 | 17.6 | 268.5 |
| Molar flow (kgmole/h) | 11972 | 3959 | 25665 | 4230 | 21435 | 2502 | 23938 |
| Molecular weight | 16.79 | 31.83 | 12.74 | 18.02 | 11.70 | 7.04 | 11.21 |
| Composition (kgmole/h) | | | | | | | |
| Water | 3986.6 | 55.5 | 4305.6 | 4228.1 | 77.4 | 10.5 | 87.9 |
| Hydrogen | 486.0 | — | 13848.6 | — | 13848.4 | 2103.7 | 15952.5 |
| Carbon monoxide | 3.9 | — | 6109.7 | 0.7 | 6109.0 | 123.4 | 6232.5 |
| Carbon dioxide | 267.5 | — | 974.8 | 0.9 | 973.9 | 187.3 | 1161.2 |
| Nitrogen | 35.9 | — | 35.9 | — | 35.9 | 8.3 | 44.3 |
| Argon | — | 11.7 | 11.7 | — | 11.7 | 5.9 | 17.6 |
| Methane | 7192.1 | — | 378.8 | — | 378.7 | 63.3 | 442.0 |
| Methanol | — | — | — | — | — | — | — |
| Oxygen | — | 3891.9 | — | — | — | — | — |
| Lights | — | — | — | — | — | — | — |
| Heavies | — | — | — | — | — | — | — |

| Stream number | 41 | 42 | 44 | 56 | 64 | 70 | 74 |
|---|---|---|---|---|---|---|---|
| Temperature (° C.) | 175 | 45 | 88 | 230 | 251 | 45 | 45 |
| Pressure (bar a) | 77.0 | 76.8 | 76.3 | 83.0 | 80.0 | 77.1 | 77.0 |
| Mass flow (tonne/h) | 16.1 | 450.7 | 703.1 | 703.1 | 703.1 | 703.1 | 228.3 |
| Molar flow (kgmole/h) | 1436 | 42871 | 65372 | 65372 | 52595 | 52595 | 7439 |

-continued

| Stream number | 41 | 42 | 44 | 56 | 64 | 70 | 74 |
|---|---|---|---|---|---|---|---|
| Molecular weight | 11.21 | 10.51 | 10.76 | 10.76 | 13.37 | 13.37 | 30.69 |
| Composition (kgmole/h) | | | | | | | |
| Water | 5.3 | 15.9 | 98.5 | 98.5 | 786.2 | 786.2 | 769.5 |
| Hydrogen | 957.2 | 28467.1 | 43462.0 | 43462.0 | 30008.6 | 30008.6 | 24.2 |
| Carbon monoxide | 374.0 | 2582.2 | 8440.6 | 8440.6 | 2731.9 | 2731.9 | 12.1 |
| Carbon dioxide | 69.7 | 3966.1 | 5057.6 | 5057.6 | 4374.9 | 4374.9 | 197.4 |
| Nitrogen | 2.7 | 735.4 | 776.9 | 776.9 | 776.9 | 776.9 | 2.4 |
| Argon | 1.1 | 282.0 | 298.6 | 298.6 | 298.6 | 298.6 | 1.5 |
| Methane | 26.5 | 6523.6 | 6939.0 | 6939.0 | 6939.0 | 6939.0 | 67.7 |
| Methanol | — | 293.4 | 293.4 | 293.4 | 6663.6 | 6663.6 | 6354.6 |
| Oxygen | — | — | — | — | — | — | — |
| Lights | — | 5.4 | 5.4 | 5.4 | 13.0 | 13.0 | 7.4 |
| Heavies | — | — | — | — | 2.2 | 2.2 | 2.2 |

| Stream number | 76 | 78 | 82 | 84 | 86 | 90 |
|---|---|---|---|---|---|---|
| Temperature (° C.) | 45 | 45 | 46 | 52 | 99 | 101 |
| Pressure (bar a) | 77.0 | 76.2 | 76.5 | 76.2 | 75.8 | 72.6 |
| Mass flow (tonne/h) | 474.8 | 24.0 | 4.0 | 4.4 | 39.7 | 22.1 |
| Molar flow (kgmole/h) | 45156 | 2286 | 220 | 231 | 3711 | 1209 |
| Molecular weight | 10.51 | 10.51 | 18.02 | 19.02 | 10.70 | 18.28 |
| Composition (kgmole/h) | | | | | | |
| Water | 16.7 | 0.8 | 220.1 | 214.7 | 11.5 | 1.1 |
| Hydrogen | 29984.4 | 1517.8 | — | — | 2474.9 | 371.2 |
| Carbon monoxide | 2719.8 | 137.7 | — | 0.0 | 511.6 | 388.2 |
| Carbon dioxide | 4177.5 | 211.5 | — | 0.6 | 280.6 | 93.2 |
| Nitrogen | 774.6 | 39.2 | — | — | 41.9 | 33.5 |
| Argon | 297.1 | 15.0 | — | — | 16.1 | 10.2 |
| Methane | 6871.3 | 347.8 | — | 0.1 | 374.2 | 310.9 |
| Methanol | 309.0 | 15.6 | — | 15.5 | — | 0.1 |
| Oxygen | — | — | — | — | — | — |
| Lights | 5.6 | 0.3 | — | — | 0.3 | 0.3 |
| Heavies | — | — | — | — | — | — |

Example 3

Example 3 is for a process according to FIG. 2, utilising two stages of methanol synthesis in which the first stage comprises an axial-flow steam-raising converter operated on a once through basis followed by a radial-flow steam-raising converter operated in a loop. The process conditions and compositions of the various streams are set out below.

| Stream number | 20 | 24 | 26 | 30 | 32 | 34 | 36 |
|---|---|---|---|---|---|---|---|
| Temperature (° C.) | 650 | 228 | 1050 | 93 | 45 | 53 | 46 |
| Pressure (bar a) | 35.4 | 39.5 | 34.0 | 30.9 | 30.9 | 30.9 | 30.9 |
| Mass flow (tonne/h) | 201.1 | 126.0 | 327.1 | 76.3 | 250.8 | 21.8 | 272.7 |
| Molar flow (kgmole/h) | 11971 | 3960 | 25665 | 4231 | 21435 | 2806 | 24241 |
| Molecular weight | 16.79 | 31.83 | 12.74 | 18.02 | 11.70 | 7.78 | 11.25 |
| Composition (kgmole/h) | | | | | | | |
| Water | 3986.4 | 55.5 | 4306.4 | 4229.0 | 77.4 | 9.0 | 86.5 |
| Hydrogen | 485.8 | — | 13848.0 | — | 13848.4 | 2347.0 | 16195.6 |
| Carbon monoxide | 3.8 | — | 6109.7 | 0.7 | 6109.2 | 58.0 | 6167.2 |
| Carbon dioxide | 267.4 | — | 974.9 | 0.9 | 974.0 | 314.2 | 1288.3 |
| Nitrogen | 35.9 | — | 35.9 | — | 35.9 | 7.8 | 43.7 |
| Argon | — | 11.7 | 11.7 | — | 11.7 | 5.9 | 17.6 |
| Methane | 7191.6 | — | 378.4 | — | 378.3 | 63.7 | 442.0 |
| Methanol | — | — | — | — | — | — | — |
| Oxygen | — | 3892.7 | — | — | — | — | — |
| Lights | — | — | — | — | — | — | — |
| Heavies | — | — | — | — | — | — | — |

| Stream number | 50 | 56 | 64 | 70 | 74 | 76 | 110 |
|---|---|---|---|---|---|---|---|
| Temperature (° C.) | 301 | 230 | 247 | 45 | 45 | 45 | 45 |
| Pressure (bar a) | 82.5 | 82.1 | 80 | 78.2 | 78.1 | 78.1 | 78.1 |
| Mass flow (tonne/h) | 10.8 | 283.5 | 283.5 | 283.5 | 107.3 | 176.2 | 440.0 |
| Molar flow (kgmole/h) | 600 | 24841 | 18447 | 18447 | 3374 | 15073 | 40697 |
| Molecular weight | 18.02 | 11.41 | 15.37 | 15.37 | 31.80 | 11.69 | 10.81 |
| Composition (kgmole/h) | | | | | | | |
| Water | 600.0 | 686.5 | 133.6 | 133.6 | 131.5 | 2.1 | 31.4 |
| Hydrogen | — | 16195.6 | 10361.9 | 10361.9 | 13.6 | 10348.3 | 28102.1 |
| Carbon monoxide | — | 6167.3 | 2412.1 | 2412.1 | 16.0 | 2396.0 | 2645.1 |
| Carbon dioxide | — | 1288.3 | 1844.3 | 1844.3 | 121.8 | 1722.5 | 4874.5 |
| Nitrogen | — | 43.7 | 43.7 | 43.7 | 0.2 | 43.5 | 435.5 |
| Argon | — | 17.6 | 17.6 | 17.6 | — | 17.5 | 174.4 |
| Methane | — | 442.0 | 442.0 | 442.0 | 6.5 | 435.5 | 4196.8 |
| Methanol | — | — | 3185.2 | 3185.2 | 3078.8 | 106.4 | 231.2 |
| Oxygen | — | — | — | — | — | — | — |
| Lights | — | — | 5.2 | 5.2 | 4.0 | 1.2 | 5.9 |
| Heavies | — | — | 1.4 | 1.4 | 1.3 | — | — |

| Stream number | 120 | 128 | 134 | 136 | 138 | 142 | 144 |
|---|---|---|---|---|---|---|---|
| Temperature (° C.) | 235 | 278 | 45 | 45 | 45 | 46 | 51 |
| Pressure (bar a) | 80.5 | 80.0 | 78.2 | 78.2 | 78.1 | 77.7 | 77.4 |
| Mass flow (tonne/h) | 616.2 | 616.2 | 133.0 | 483.3 | 43.2 | 7.1 | 7.8 |
| Molar flow (kgmole/h) | 55770 | 49299 | 4603 | 44696 | 3999 | 396 | 413 |
| Molecular weight | 11.05 | 12.50 | 28.88 | 10.81 | 10.81 | 18.02 | 18.86 |
| Composition (kgmole/h) | | | | | | | |
| Water | 33.5 | 1144.0 | 1109.6 | 34.5 | 3.1 | 396.0 | 389.2 |
| Hydrogen | 38450.3 | 30873.8 | 10.6 | 30863.5 | 2761.3 | — | — |
| Carbon monoxide | 5041.2 | 2911.6 | 6.6 | 2905.1 | 259.9 | — | 0.0 |
| Carbon dioxide | 6597.0 | 5490.9 | 137.4 | 5353.5 | 479.0 | — | 1.3 |
| Nitrogen | 479.0 | 478.9 | 0.7 | 478.2 | 42.8 | — | — |
| Argon | 191.9 | 191.9 | 0.3 | 191.6 | 17.1 | — | — |
| Methane | 4632.3 | 4632.2 | 23.1 | 4609.1 | 412.4 | — | 0.1 |
| Methanol | 337.6 | 3564.7 | 3310.7 | 253.9 | 22.7 | — | 22.6 |
| Oxygen | — | — | — | — | — | — | — |
| Lights | 7.1 | 8.4 | 1.9 | 6.5 | 0.6 | — | — |
| Heavies | — | 2.3 | 2.3 | — | — | — | — |

| Stream number | 146 | 150 |
|---|---|---|
| Temperature (° C.) | 52 | 53 |
| Pressure (bar a) | 76.3 | 73.8 |
| Mass flow (tonne/h) | 42.6 | 20.8 |
| Molar flow (kgmole/h) | 3982 | 1176 |
| Molecular weight | 10.69 | 17.65 |
| Composition (kgmole/h) | | |
| Water | 9.9 | 0.9 |
| Hydrogen | 2761.3 | 414.2 |
| Carbon monoxide | 259.9 | 201.8 |
| Carbon dioxide | 477.7 | 163.5 |
| Nitrogen | 42.8 | 35.0 |
| Argon | 17.1 | 11.2 |
| Methane | 412.2 | 348.5 |
| Methanol | — | 0.1 |
| Oxygen | — | — |
| Lights | 0.6 | 0.6 |
| Heavies | — | — |

A comparison of the Examples is given below.

| Example | Methanol make (kmol/h) |
|---|---|
| 1 | 6426 |
| 2 Comparative | 6370 |
| 3 | 6412 |

In the Examples, the total methanol make consists of the methanol content of the crude methanol stream plus the methanol recovered from the purge gas washing unit in the purge gas wash stream. Both examples 1 and 3 are superior to the comparative arrangement in Example 2.

The invention claimed is:

1. A process for synthesising methanol comprising the steps of:

(i) passing a hydrocarbon feedstock to a synthesis gas generation unit to form a synthesis gas containing hydrogen, carbon monoxide, carbon dioxide and steam, wherein the synthesis gas contains 2.5 to 7% by volume of carbon dioxide on a wet basis;

(ii) cooling the synthesis gas in one or more stages of heat exchange and recovering a process condensate from the cooled synthesis gas to form a make-up gas having a stoichiometry value R in the range of 1.70 to 1.94;

(iii) passing a feed gas comprising the make-up gas to a methanol synthesis unit comprising one or more methanol synthesis reactors containing a copper methanol synthesis catalyst, and;

(iv) recovering a purge gas and a crude methanol product from the methanol synthesis unit, wherein a hydrogen-rich gas is recovered from the purge gas and combined with the make-up gas, and a stream of water or steam is added to the feed gas to the methanol synthesis unit.

2. The process according to claim 1, wherein the synthesis gas generation unit comprises a partial oxidation unit having one or more catalytic, or non-catalytic, partial oxidation vessels, or a gasification unit containing one or more gasifiers, or a reforming unit comprising one of more catalytic steam reformers.

3. The process according to claim 1, wherein the synthesis gas generation unit comprises an autothermal reformer.

4. The process according to claim 1, wherein the synthesis gas generation unit comprises an adiabatic pre-reformer and autothermal reformer connected in series.

5. The process according to claim 1, wherein the hydrocarbon feedstock comprises natural gas.

6. The process according to claim 4, wherein the hydrocarbon feedstock is pre-reformed in an adiabatic pre-reformer upstream of the autothermal reformer with steam at a steam to carbon ratio in the range of 0.3 to 3.

7. The process according to claim 1, wherein the feed gas has a stoichiometry number R which is higher than that of the make-up gas.

8. The process according to claim 1, wherein the stream of water or steam is added to the feed gas to the methanol synthesis unit in an amount of 0.1 to 6 mole % on make-up gas.

9. The process according to claim 1, wherein a stream of water is added to the feed gas to the methanol synthesis unit, and at least a portion of the stream of water added to the feed gas is recovered from a purge gas washing step.

10. The process according to claim 1, wherein the methanol synthesis unit comprises one, two or more methanol synthesis reactors each containing a bed of methanol synthesis catalyst.

11. The process according to claim 1, wherein an unreacted gas mixture separated from a product gas mixture recovered from one methanol synthesis reactor is returned to the same or a different methanol synthesis reactor.

12. The process according to claim 1, wherein the methanol synthesis unit comprises a first methanol synthesis reactor and a second methanol synthesis reactor connected in series, wherein the first methanol synthesis reactor operates on a once-through basis and gas fed to the second methanol synthesis reactor consists of all of an unreacted gas stream recovered from the first methanol synthesis reactor and a recycle gas stream recovered from the second methanol synthesis reactor.

13. The process according to claim 1, wherein the methanol synthesis unit comprises a first methanol synthesis reactor and a second methanol synthesis reactor connected in series, wherein a portion of an unreacted gas stream recovered from the first methanol synthesis reactor is recycled to the first methanol synthesis reactor and a portion of an unreacted gas stream recovered from the second methanol synthesis reactor is recycled to the second methanol synthesis reactor.

14. The process according to claim 1, wherein the methanol synthesis unit comprises a first methanol synthesis reactor and a second methanol synthesis reactor connected in series, wherein a portion of an unreacted gas stream recovered from the second methanol synthesis reactor is recycled to the first methanol synthesis reactor.

15. The process according to claim 12, wherein the first methanol synthesis reactor is an axial-flow steam-raising converter and the second methanol synthesis reactor is an axial-flow steam-raising converter, a radial-flow steam-raising converter, a gas-cooled converter or a tube-cooled converter.

16. The process according to claim 1, wherein the copper methanol synthesis catalyst comprises copper, zinc oxide and alumina.

17. The process according to claim 1, wherein a carbon-rich off gas obtained by separation of the hydrogen-rich gas from the purge gas is used as a fuel in a fired heater to heat one or more feed streams to the synthesis gas generation unit, or is exported to a separate process.

18. The process according to claim 11, wherein a $CO_2$ removal unit is included to recover carbon dioxide from the unreacted gas mixture and exported for use in a separate process or purified and sequestered or used for enhanced oil recovery.

19. The process according to claim 1, wherein a carbon dioxide stream is recovered from the crude methanol and used in an external chemical synthesis process or for enhanced oil recovery or sequestered in a carbon capture and storage unit.

20. The process according to claim 1, wherein the crude methanol is subjected to one or more steps of distillation to produce a purified methanol product.

21. The process according to claim 1, wherein the synthesis gas contains 3 to 5% by volume of carbon dioxide on a wet basis.

22. The process according to claim 13, wherein the first methanol synthesis reactor is an axial-flow steam-raising converter and the second methanol synthesis reactor is an axial-flow steam-raising converter, a radial-flow steam-raising converter, a gas-cooled converter or a tube-cooled converter.

23. The process according to claim 14, wherein the first methanol synthesis reactor is an axial-flow steam-raising converter and the second methanol synthesis reactor is an axial-flow steam-raising converter, a radial-flow steam-raising converter, a gas-cooled converter or a tube-cooled converter.

* * * * *